United States Patent [19]

Imamura et al.

[11] 4,347,323

[45] Aug. 31, 1982

[54] GLYCEROL KINASE FROM *STREPTOMYCES CANUS*

[75] Inventors: Shigeyuki Imamura; Tohru Matsumoto; Naoki Muto; Hideo Misaki, all of Shizuoka, Japan

[73] Assignee: Toyo Jozo Kabushiki Kaisha, Shizuoka, Japan

[21] Appl. No.: 154,029

[22] Filed: May 28, 1980

[30] Foreign Application Priority Data

Jun. 6, 1979 [JP] Japan .................................. 54-71459

[51] Int. Cl.³ ........................ C12N 9/12; C12R 1/465; C12Q 1/48
[52] U.S. Cl. .................................... 435/194; 435/15; 435/886
[58] Field of Search .................... 435/15, 886, 194, 89, 435/193

[56] References Cited

U.S. PATENT DOCUMENTS 3,677,901 7/1972 Bergmayer et al. ................. 435/194
4,152,209 5/1979 Nishino et al. ....................... 435/194

OTHER PUBLICATIONS

Colowick, S. P., *Methods in Enzymology*, Academic Press, 1962, pp. 476–479, vol. 5.
Bublitz et al., Synthesis of Phosphatides in Isolated Mitochondria, *J of Biol. Chem.* 1954, vol. 211, pp. 951–961.
Hayashe et al., Purification and Properties of Glycerol Kinase from *E. coli*, *J. of Biol. Chem.*, 1967, vol. 24, pp. 1030–1035.
Barman T. E. *Enzyme Handbook*, Springer-Vertag, 1969, vol. 1, pp. 401–402.
Boyer et al., *The Enzymes*, Academic Press, 1962, vol. 6, p. 78.

*Primary Examiner*—David M. Naff
*Assistant Examiner*—Kathleen S. McCowin
*Attorney, Agent, or Firm*—Young & Thompson

[57] ABSTRACT

A novel glycerol kinase is produced from the microorganism *Streptomyces canus* FERM-P No. 4977 and is useful as a diagnostic reagent for assay of triglycerides and glycerol in body fluids such as serum.

2 Claims, 3 Drawing Figures

GLYCEROL KINASE FROM *STREPTOMYCES CANUS*

This invention relates to a novel glycerol kinase and a method for its production.

Glycerol kinase has been hitherto known as an enzyme which catalyzes the following reaction:

ATP+glycerol→ADP+L-α-glycerophosphate

[EC 2.7.1.30 ATP: glycerol phosphate transferase, common name: glycerol kinase].

Hitherto-known glycerol kinase (hereinafter referred to as GK) is an enzyme from *Candida mycoderma* [Biochem. Z., 329, 320 (1957), ibid., 333, 471 (1961)], an enzyme from *Escherichia coli* [J. Biol. Chem., 242, 1030 (1967)] and an enzyme from pigeon liver [Method in Enzymology, Vol. 5, 476 (1962), Biochem. Z., 329, 320 (1957), J. Biol. Chem., 211, 951 (1954)].

We have found that a Streptomyces strain A 2408 isolated from a soil sample from a soybean field in Kakegawa, Shizuoka, Japan, produces an enzyme which catalyzes a reaction with glycerol and ATP to form ADP and L-α-glycerophosphate, in its cells, and have purified it as an electropholetically homogeneous enzyme. As a result, the said enzyme belongs to the GK group; however, its physico-chemical and biochemical properties are hitherto unknown and hence it is a novel GK.

The taxonomical properties of the said Streptomyces strain A 2408 are as follows:

I. Morphological properties

Color of matured spore-bearing aerial hyphae are brownish gray to grayish brown. Yellowish brown substrate mycelia. Produces yellowish brown soluble pigment.

Observations on starch-inorganic agar at 30° C. for 10 days are illustrated as follows. The same morphological features are observed on oatmeal agar and glycerol-asparagine agr.

The aerial hyphae are 0.6–0.8μ in diameter, straight or wavy, grow with simple branching and form many spore chains. The spore chains form spirals with 3-5 loose coils, in the form of a hook, loop or other bent shape.

The shapes of the spores are globose or oval, 0.8–1.0×1.0–1.5μ, with spiny surfaces.

The substrate mycelia are branched, and grow with wavy or other bent shapes, 0.5–0.6μ in diameter, with ordinarily no splitting of the hyphae and bearing of spores.

There is no formation of flagellar spores and sporangia.

II. Composition of diaminopimeric acid

L-diaminopimeric acid was detected.

III. Characteristics on various media

Observations on various media at 30° C. for 20 days are illustrated in Table 1. [Color indication is based on "Color Harmony Manual, 4th Ed. 1958" (Container Corp. of America, USA)]

IV. Physiological properties

A. Growth temperature: 12°–45° C.
B. Liquefaction of gelatin: positive
C. Starch hydrolysis: positive
D. Skim milk: peptonization positive, coagulation negative.
E. Formation of melanin-like pigment: negative.
F. Utilization of carbon sources Utilizes: L-arabinose, D-fructose, D-glucose, i-inositol, D-mannitol, raffinose, L-rhamnose, sucrose and D-xylose.

TABLE 1

| Medium | growth | color of substrate mycelium | aerial mycelium | soluble pigment |
| --- | --- | --- | --- | --- |
| sucrose-nitrate agar | moderate to good | golden brown (3 pi) | moderate to good: bisque (3 ec) | none |
| glucose-asparagine agar | moderate | mustard brown (2 pi) | poor to moderate: natural (3 dc) to bisque (3 ec) | none |
| glycerol-asparagine agar | good | clove brown (3 pl) to golden brown (3 pi) | good: beige (3 ge) to beige brown (3 ig) | none |
| starch-inorganic salt agar | good | golden brown (3 pi) to clove brown (3 pl) | good: beige (3 ge) to silver gray (3 fe) | none |
| tylosine agar | good | golden brown (3 pi) to clove brown (3 pl) | good: beige (3 ge) to beige brown (3 ig) | none to pale light brown (4 ng) |
| oatmeal agar | good | golden brown (3 pi) | good: beige (3 ge) to beige brown (3 ig) | none |
| yeast extract-malt extract agar | good | golden brown (3 pi) | good: natural (3 dc) to silver gray (3 fe) | none |
| glycerol nitrate agar | good | clove brown (3 pl) | good: natural (3 dc) to beige (3 ge) | clove brown (3 pl) |
| glycerol-starch-glutamate agar | good | clove brown (3 pl) | good: beige (3 ge) to convert tan (2 ge) | clove brown (3 pl) |
| Benett agar | good | golden brown (3 pi) | good: natural (3 dc) to silver gray (3 fe) | none |
| Emerson agar | moderate | mustard gold (2 pe) | little: white (a) | none |
| Nutrient agar | poor to little | colorless to light wheat (2 ea) | none | none |

As hereinabove illustrated, the present microorganism strain A 2408 belongs to Streptomyces by virtue of the characteristics of aerial mycelia having spore chains grown from nondivisional true substrate mycelia, the diameter of the mycelia, the spore size, and the presence of L-type diaminopimelic acid. The strain A 2408 has the following characteristics:

The color of the aerial mycelia is brownish gray to grayish brown. The spore chain is 3-5 loosely coiled spirals. The surface of spore has spines. The color of the substrate mycelia is yellowish brown. There is formation of a yellowish brown soluble pigment. The utilization of sugar is broad. There is no formation of melanine-like pigment. A microorganism having these characteristics can be identified as *Streptomyces canus* (Heinemann et al.) [Antibiotics and Chemotherapy, 3, 1239–1242 91953)] in International Streptomyces Project (ISP) [Inter. J. System. Bacteriol., 18 (2), 95 (1968)]. Comparison with the present strain A 2408 and *Streptomyces canus* ISP 5017 showed a resemblance of morphological, cultural and physiological properties.

Therefore, the present strain A 2408 is referred to as *Streptomyces canus* A 2408. This strain was deposited in the Institute for Microbial Industry and Technology, Japan, as permanent collection FERM-P No. 4977.

We have found that GK produced by *Streptomyces canus* A 2408 is a novel enzyme having the physico-chemical and biochemical properties hereinafter illustrated.

GK can be used as a research reagent or a diagnostic reagent for the metabolism of triglycerides in body fluids such as serum.

The object of the present invention, therefore, is to provide a novel GK and a method for its production.

Figure 1:
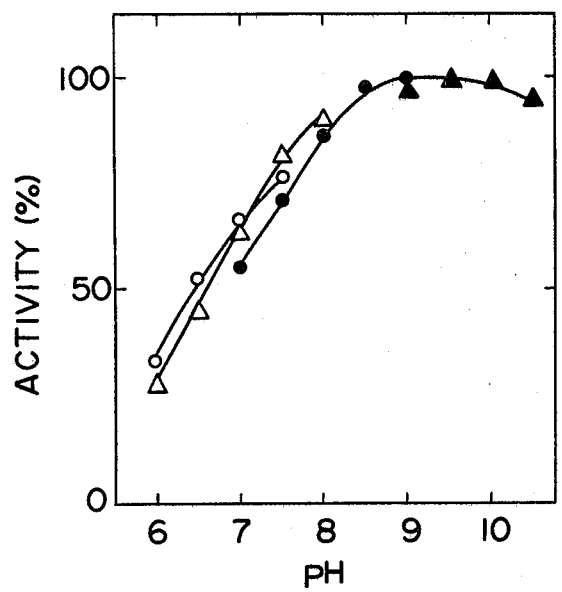
FIG. 1 is the optimum pH curve of the present GK.

As a microorganism useful in the process of the present invention, can be mentioned, for example, the hereinbefore-described Streptomyces; but the invention is not limited to microorganism, as there can be used the present GK-producing microorganism and its mutant strains.

The novel GK of the present invention can be produced by culturing a GK-producing microorganism such as a GK-producing strain belonging to the genus Streptomyces, in a conventional medium for enzyme production. Cultivation is usually liquid cultivation and submerged aeration culture is advantageous for industrial production.

Conventional nutrient media for microorganisms can be used. As for carbon sources, any assimilable carbon source, especially glycerol, can be used advantageously. Other carbon sources such as glucose, sucrose, lactose, starch or molasses can also be used. As nitrogen sources, assimilable nitrogen sources such as corn steep liquor, soybean powder, cotton seed powder, dry yeast, casein hydrolyzate, yeast extract, fish meal extract and peptone can be used. Phosphates, sulfates and inorganic salts of magnesium, calcium, potassium, iron, manganese or zinc can be used if necessary.

The cultivation temperature can be selected within the conditions for growth of microorganisms and production of GK, and is preferably 25°–30° C. The cultivation time depends on conditions. Cultivation should be terminated at maximum production of GK and the cultivation time is usually 1–3 days.

The present enzyme can be isolated from mycelia. Cultured broth is centrifuged to collect cultured mycelia which are sonicated by ultrasonics, then centrifuged to yield a supernatant solution. The said supernatant solution is salted-out using for example ammonium sulfate (hereinafter designated as AS) or sodium sulfate to separate impurities. The supernatant is subjected to further salting-out, and centrifuged to obtain a precipitate containing GK. The GK precipitate is further purified by desalting with Sephadex G-25 (tradename, Pharmacia Co.), Biogel P-2 (tradename, Biorad Corp.), a dialyzing membrane or hollow fibers, and subjected to ion-exchange chromatography such as that using DEAE-cellulose. The thus-obtained GK fraction is desalted and concentrated by use of an ultrafiltration membrane such as Amicon XM-50 (tradename, Amicon Co.) The desalted fraction is subjected to adsorption chromatography such as that using a calcium phosphate gel column to separate impurities, and is thereafter gradiently eluted with a phosphate buffer. The GK-containing fraction is desalted and concentrated by use of an ultra-filtration membrane such as Amicon XM-50. The said concentrate is subjected to gel-filtration chromatography using for example Biogel P-200 (Biorad Co.) or Sephadex G-150 (Pharmacia Co.), and then the GK fraction is lyophilized.

The GK obtained by the above purification procedure has the following physico-chemical and biochemical properties:

1. Enzyme assay

| | |
|---|---|
| 0.2 M tris-HCl buffer (pH 9.0) | 0.4 ml |
| 0.1 M glycerol | 0.05 ml |
| 10 mM ATP | 0.1 ml |
| 10 mM MgCl$_2$ | 0.1 ml |
| 0.25% nitrotetrazolium blue | 0.1 ml |
| 1% bovine serum albumin | 0.14 ml |
| 10 mM NAD | 0.1 ml |
| 0.05% phenazine methosulfate | 0.01 ml |
| glycerophosphate dehydrogenase (Boehringer Co., 2 mg/ml, 65 U/mg) | 5 μl |

The above mixture (1 ml) is preincubated at 37° C. for 5 minutes and GK solution (50 μl) [diluted with GL-buffer (10 mM phosphate buffer containing 10 mM glycerol, pH 7.5)] is added thereto and incubated at 37° C. for 10 minutes. The reaction is terminated by adding 0.1 N HCl and the reaction medium is assayed at 550 nm to measure the absorbance ($A_{550\ nm}$).

One unit of GK is defined as liberating 1 mole of glycero-3-phosphate per minute.

Enzyme activity is calculated by the following equation:

$$\text{Enzyme activity } (U/ml) = \frac{\Delta A \times \text{dilution ratio}}{0.50 \times 10} \times \tfrac{1}{4}$$

$$= \frac{\Delta A}{2} \times \text{dilution ratio}$$

2. Physico-chemical and biochemical properties

Enzyme action: catalyzes at least the following reaction.

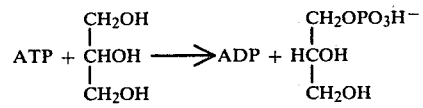

Molecular weight: 72000±7200
72000: measured by Sephadex G-100.
65000: measured by SDS polyacrylamide.
Isoelectric point: pH 4.5.
Km value:

| | |
|---|---|
| glycerol: | $4.8 \times 10^{-5}$ M |
| dihydroxyacetone: | $6.6 \times 10^{-4}$ M |
| D-glyceraldehyde: | $3.5 \times 10^{-4}$ M |
| ATP: | $2 \times 10^{-4}$ M |

Substrate specificity (i) specificity for glycerol, dihydroxyacetone phosphate and D-glyceraldehyde:

(assay method)
Reaction mixture:

| | |
|---|---|
| 0.2 M tris-HCl buffer (pH 9.0) | 0.4 ml |
| 0.1 M glycerol, dihydroxyacetone phosphate or D-glyceraldehyde | 0.05 ml |
| 10 mM ATP | 0.1 ml |
| 10 mM MgCl$_2$ | 0.1 ml |
| distilled water | 0.3 ml |

The reaction mixture (0.95 ml) is preincubated at 37° C. for 3 minutes, and the enzyme solution (dissolved in 10 mM phosphate buffer, pH 7.5, 0.05 ml) is added thereto. Then the mixture is incubated at 37° C. for 10 minutes. The reaction is stopped by boiling for 3 minutes. After cooling to 37° C., the amount of ADP is assayed. ADP is assayed by adding an ADP-assay solution (2.0 ml) comprising the following mixture:

| | |
|---|---|
| 0.1 M phosphate buffer (pH 7.5) | 0.1 ml |
| 0.2 M dimethylglutarate-NaOH buffer (pH 7.5) | 0.1 ml |
| peroxidase (0.5 mg/ml) | 0.1 ml |
| 0.2% phenol | 0.1 ml |
| 0.3% 4-aminoantipyrine | 0.1 ml |
| 10 mM MnCl$_2$ | 0.05 ml |
| 10 mM thiamine pyrophosphate | 0.03 ml |
| 1 mM FAD | 0.01 ml |
| 10 mM phosphoenol pyruvate | 0.1 ml |
| pyruvate oxidase (100 U/ml; Toyo Jozo Co.) | 0.05 ml |
| pyruvate kinase (4400 U/ml; Sigma Chem. Co.) | 1 μl |
| distilled water | 1.26 ml |

The reaction mixture is incubated at 37° C. for 15 minutes. Color formation is measured at 550 nm to calculate the substrate specificity.

| Substrate | Relative activity |
|---|---|
| glycerol | 100% |
| dihydroxyacetone | 74% |
| D-glyceraldehyde | 20% |

(ii) specific activity for nucleotide:

ATP>CTP>ITP>>GTP, UTP (assay method)

In assay method (i) hereinabove, 10 mM ATP is replaced by CTP, ITP, GTP and UTP and measures the formed glycero-3-phosphate. As hereinbelow illustrated all the nucleotides assayed can be a substrate, and especially high specificity for ATP and CTP was observed.

| Substrate | Relative activity (%) |
|---|---|
| ATP | 100 |
| CTP | 92 |
| ITP | 47 |
| GTP | 19 |
| UTP | 18 |

Figure 2:
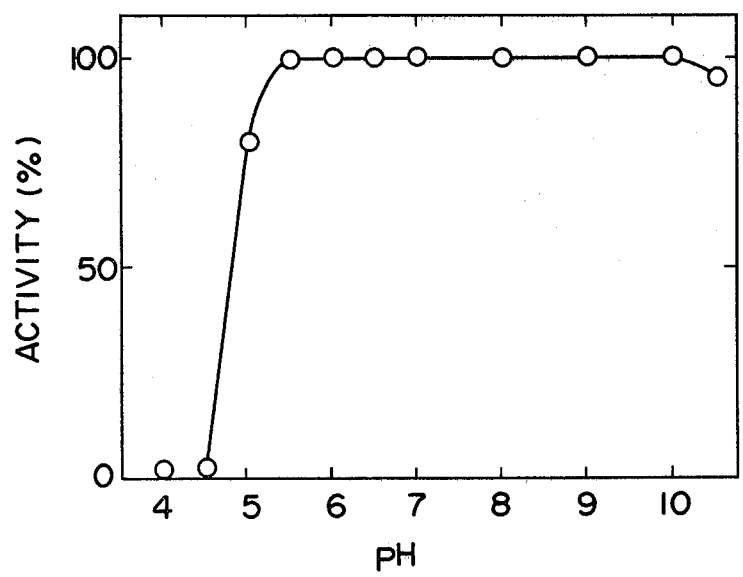
FIG. 2 is the pH-stability curve of the present GK.

Optimum pH: pH 9–10 as shown in FIG. 1. [In FIG. 1, ○—○: dimethylglutarate-NaOH buffer (pH 6–7.5), •—•: tris-HCl buffer (pH 7–9), △—△: phosphate buffer (pH 6–8), ▲—▲: glycine-NaOH buffer (pH 9–10.5)]

pH stability: pH 5.5–10 as shown in FIG. 2.

Dimethylglutarate buffer (pH 4–7) and glycine-NaOH buffer (pH 10–10.5), each containing 10 mM glycerol are used. Incubation is carried out at 37° C. for 60 minutes.

Effect of metal ions and p-chloromercuribenzoate (PCMB)

| | | Relative Activity (%) | |
|---|---|---|---|
| Reagent | Concentration | without Mg++ | with 1 mM Mg++ |
| None | — | 5 | 100 |
| MgCl$_2$ | 1.0 mM | 100 | 100 |
| CaCl$_2$ | 1.0 mM | 0 | 54 |
| MnCl$_2$ | 1.0 mM | 6 | 14 |
| PCMB | 5.0 × 10$^{-6}$M | — | 13 |
| PCMB | 7.5 × 10$^{-6}$M | — | 0 |

GK of the present invention is activated by Mg++ and inhibited by Ca++ and Mn++. 7.5×10$^{-6}$ M of PCMB completely inhibits the activity of the present GK.

Figure 3:
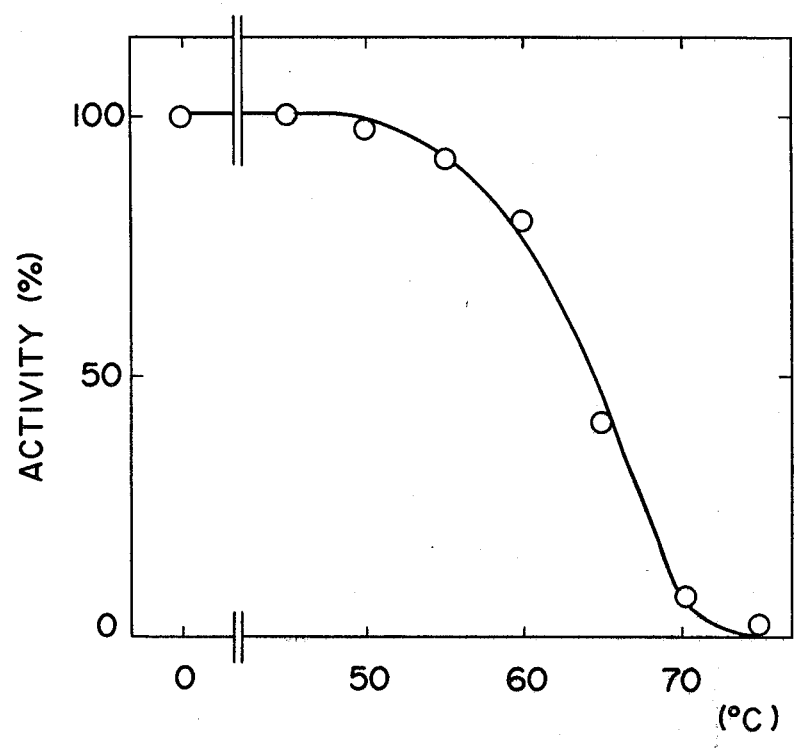
FIG. 3 is the heat stability curve of the present GK.

Heat stability: stable up to 45° C. as shown in FIG. 3.

Assay: 10 mM phosphate buffer (pH 7.8) containing 10 mM glycerol. Incubation of the samples at 45°–75° C., each for 10 minutes.

As hereinabove illustrated, the enzyme of the present invention is an enzyme which catalyzes a reaction from glycerol and ATP to ADP and L-α-glycerate.

A comparison between known glycerol kinase of *Candida mycoderma* GK (hereinafter designated C.My.-GK), *Escherichia coli* GK (hereinafter designated E.Co-GK) and pigeon heart GK (hereinafter designated Pig.-GK) and GK of the present invention, is as follows:

The molecular weight of E.Co-GK is 300,000 and that of C.My.-GK is 250,000 (a tetramer of molecular weight of 60,000); whereas the GK of the present invention is a monomer of a molecular weight of about 70,000. The pH stability is pH 6.5–7 for E.Co-GK, pH 4.5–5.5 for Pig.-GK and pH 6.7 for C.My.-GK, whereas the pH is 5.5–10 for the present GK. Since the reaction requiring ATP requires a divalent metal ion, the above GK also requires Mg++; however Mn++ can be used for E.Co-GK and Pig.-GK, whereas Mn++ strongly inhibits the present GK.

Furthermore, the respective substrate specificities differ from each other. E.Co-GK exhibits nearly twice the activity for dihydroxyacetone phosphate as compared with glycerol; whereas the present GK shows higher specificity for glycerol than that of dihydroxyacetone phosphate. E.Co-GK acts only for ATP, and the present GK acts for ATP and CTP, also for ITP, GTP and UTP. As a result, the molecular weight, pH-stability, requirement for divalent metal ion and substrate specificity together show that the present glycerol kinase is novel.

The GK of the present invention can be used as a diagnostic enzyme. For example, the present GK can be used for assaying triglycerides and glycerol by reacting with triglycerides and lipoproteinlipase, incubating the reaction mixture with GK and ATP to form glycero-3-phosphate which is further incubated with glycero-3-phosphate oxidase, then measuring the consumed oxygen or liberated hydrogen peroxide.

The following example illustrates the present invention but is not to be construed as limiting.

EXAMPLE

An aqueous culture medium (100 ml) (pH 7.0) containing peptone 1.0%, glycerol 1.5%, $K_2HPO_4$ 0.1%, $MgSO_4$ 0.05% and KCl 0.20% in a 500 ml Erlenmeyer flask was sterilized at 120° C. for 20 minutes. *Streptomyces canus* A 2408 FERM-P No. 4977 was inoculated therein and cultured at 26° C. for 3 days. The cultured broth was inoculated in a 30 l.-jar fermenter containing the same medium (20 l.), and aerobically cultured at 26° C. for 40 hours, 300 r.p.m., with aeration of 20 l./min. Two liters of the cultured broth was centrifuged (15,000 r.p.m., for 10 minutes) at 4° C. to collect mycelia. The mycelia was suspended in GL buffer (800 ml) and sonicated at 0° C. for 5 minutes by ultrasonic apparatus (Kubota Insonator 200M, tradename).

The solution was centrifuged at 4° C. for 10 minutes at 15,000 r.p.m. to obtain a supernatant (760 ml). After adding 5% protamine solution (23.0 ml), impurities were precipitated off by centrifuging at 4° C., 5000 r.p.m. for 10 minutes. To a saturated solution of ammonium sulfate (pH 7.5, 1125 ml) was added the supernatant (750 ml) and the mixture was centrifuged at 4° C., 15,000 r.p.m. for 10 minutes to collect the precipitate. Further saturated AS (pH 7.5, 37.2 ml) was added to the solution of the said precipitate in 62 ml of GL buffer to precipitate the impurities. The supernatant (82 ml) was obtained by centrifuging at 4° C., 15,000 r.p.m. for 10 minutes, then saturated AS (pH 7.5, 20.5 ml) was added. Further centrifuging at 4° C., 15,000 r.p.m. for 10 minutes gave the precipitate.

The precipitate was dissolved in GL-buffer (11.0 ml) and the solution was charged on a column of Sephadex G-25 (3×30 cm) packed with the same buffer, then eluted with the same buffer at 25° C., at a flow rate of 40 ml/hour. The fractions showing absorption at 280 nm were collected (about 21 ml). These were charged on a column of DEAE-cellulose (2.2×17 cm) packed with GL-buffer, washed with GL-buffer (80 ml) (flow rate 25 ml/hour, 5.8 ml/fraction), thereafter impurities were eluted off with GL-buffer containing 0.1 M KCl (flow rate 25 ml/hour, 5.8 ml/fraction). Active fractions Nos. 63–79 were collected by linear gradient elution with a GL-buffer containing 200 ml of 0.1 M KCl and a GL-buffer containing 200 ml of 0.4 M KCl (flow rate 25 ml/hour, each fraction 5.8 ml). A combined active eluate (98 ml) was desalted and concentrated with Amicon XM-50 at 4° C., for 4 hours to obtain the concentrated solution (10 ml). The concentrate was charged on a column of calcium phosphate gel (2.0×17.2 cm) packed with GL-buffer, washed with GL-buffer (100 ml) and eluted with a linear gradient of GL-buffer 200 ml to 100 mM phosphate buffer containing 200 ml of 100 mM glycerol (flow rate 25 ml/hour, each fraction 6 ml). Active fractions Nos. 48–58 were collected and the combined solution was concentrated with Amicon XM-50 to obtain the concentrate (2 ml). The said concentrate was charged on a column of Biogel P-200 (3×60 cm) packed with GL-buffer, eluted with the same buffer (flow rate 25 ml/hour, each fraction 6 ml) and the active fractions Nos. 17–20 were collected, which were combined and lyophilized to obtain the purified GK (specific activity: 57.6 U/mg, 16.9 mg-protein).

What is claimed is:

1. Glycerol kinase having the following properties:
   (1) enzyme action: catalyzes at least the following reaction:

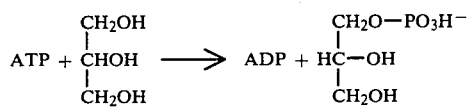

(2) molecular weight: 72000±7200
   (3) isoelectric point: 4.5
   (4) Km value:

| | |
|---|---|
| glycerol | $4.8 \times 10^{-5}$M |
| dihydroxyacetone | $6.6 \times 10^{-4}$M |
| D-glyceraldehyde | $3.5 \times 10^{-4}$M |
| ATP | $2 \times 10^{-4}$M |

(5) specificities for nucelotides: ATP>CTP>ITP>>GTP, UTP
   (6) optimum pH: pH 9–10
   (7) pH stability: pH 5.5–10
   (8) effect of metal ions: stimulated by Mg++, inhibited by Ca++ and Mn++
   (9) heat stability: stable up to 45° C.

2. A process for the production of glycerol kinase, which comprises culturing *Streptomyces canus* FERM-P No. 4977 in a nutrient medium containing carbon and nitrogen sources and inorganic salt, and then isolating the thus-produced glycerol kinase from the cultured medium.

* * * * *